United States Patent [19]

Palmer

[11] Patent Number: 5,714,480
[45] Date of Patent: Feb. 3, 1998

[54] TREATING CARDIOVASCULAR DISEASE WITH STEROIDAL 5-ALPHA-REDUCTASE INHIBITORS

[75] Inventor: Robert Howard Palmer, Ardmore, Pa.

[73] Assignee: SmithKline Beecham Corporation, Philadelphia, Pa.

[21] Appl. No.: 718,564

[22] PCT Filed: Mar. 30, 1995

[86] PCT No.: PCT/US95/04023

§ 371 Date: Dec. 26, 1996

§ 102(e) Date: Dec. 26, 1996

[87] PCT Pub. No.: WO95/26731

PCT Pub. Date: Oct. 12, 1995

[30] Foreign Application Priority Data

Mar. 31, 1994 [GB] United Kingdom ............... 9406592

[51] Int. Cl.[6] .................. A01N 45/00; A61K 31/56
[52] U.S. Cl. .................................................. 514/169
[58] Field of Search ............................................ 514/169

[56] References Cited

U.S. PATENT DOCUMENTS 5,212,166   5/1993   Panzeri et al. ............ 514/176
5,422,371   6/1995   Liao et al. ................. 514/560

OTHER PUBLICATIONS

Transactions of the American Clinical and Climatological Assoc. 106th Meeting vol. CV Halushka et al., The Gordon Wilson Lecture *Regulation of Thromboxane A2 Receptors* . . . pp. 95–103, 1994.

*Primary Examiner*—Marianne M. Cintins
*Assistant Examiner*—Dwayne C. Jones
*Attorney, Agent, or Firm*—Wayne J. Dustman; Charles M. Kinzig; Edward T. Lentz

[57] ABSTRACT

Invented is a method of treating cardiovascular disease by employing a steriod 5-alpha-reductase inhibiting compound.

14 Claims, No Drawings

TREATING CARDIOVASCULAR DISEASE WITH STEROIDAL 5-ALPHA-REDUCTASE INHIBITORS

This application is a 371 of PCT/US95/04023 filed on Mar. 30, 1995, published as WO95/26731 Oct. 12, 1995.

This invention relates to a method of treating cardiovascular disease by employing a steroid 5-α-reductase inhibiting compound. Advantageously the method of this invention employs 17β-(N-t-butylcarboxamide)-androst-3,5-diene-3-carboxylic acid in the treatment of cardiovascular disease.

BACKGROUND OF THE INVENTION

The class of steroidal horomones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, ache vulgaris, seborrhea, female hirsutism, prostatic adenocarcinoma, and benign prostatic hypertrophy are correlated with elevated androgen levels. Additionally, the incidence of male pattern baldness has been associated with high androgen levels.

Testosterone (T) is the principal androgen secreted by the testes and is the primary androgenic steroid in the plasma of males. It now is known that 5-α-reduced androgens are active hormones in some tissues such as the prostate and sebaceous gland. Circulating testosterone thus serves as a prohormone for dihydrotestosterone (DHT), its 5-α-reduced analogue in these tissues but not in others such as muscle and testis. Steroid 5-α-reductase is a NADPH-dependent enzyme that converts testosterone to DHT. The importance of this enzyme in male development was dramatically underscored by discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in various disease states has stimulated many efforts to synthesize inhibitors of this enzyme.

The fast inhibitor described was 4-androsten-3-one-17β-carboxylic acid by Hisa and Voight in 1973. *J. Invest. Dermat*, 62:224–227. (4R)-5,10-seco-19-norpregna-4,5-diene-3,10,20-triane was the next inhibitor to be described and also has found utiltiy as an affinity label for 5-α-reductase. Robaire, B., et al., (1977), *J. Steroid Biochem.* 8:307–310. (5a,20-R)-4-diazo-21-hydroxy-20-methlypregnan-3-one has been reported as a potent, time-dependent inhibitor of steroid 5-α-reductase. Blohm, T. R., et al., (1980), *Biochem. Biophys. Res. Comm.* 95:273–280; U.S. Pat. No. 4,317,817, Mar. 2, 1982. 17β-N,N-diethylcarbomoyl-4-methyl-4-aza-5-α-androstan-3-one is exemplary of a group of 4-aza steroid inhibitors of steroid 5-α-reductase described in U.S. Pat. No. 4,377,584 which issued Mar. 22, 1983, and in Liang, T., et al., (1983), *J. Steroid Biochem.* 19, 385–390. 17a-acetoxy-6-methylenepregn-4-ene-3,20-dione also has been shown to be a time-dependent inactivator of steroid 5-α-reductase. Petrow, V., et al., (1981), *Steroids* 38:121–140.

Among the most potent inhibitors identified to date are 3-carboxy-androsta-3,5-diene steroidal derivatives and 3-carboxy A ring aryl steroidal derivatives.

Additional 5-α-reductase inhibitors known in the art are;

1. *Bioinorganic Chemistry*, 17, pp. 372–376 (1986), by B. W. Metcalf, et al. describes the inhibition of human steroid 5-α-reductase (EC 1.3.1.30) by 3 androstene-3-carboxylic acids;

2. *Biochemistry* (1990) Vol. 29, pp. 2815–2824, by M. A. Levy, et al. M. A. Levy, et al. describes the mechanism of enzyme inhibitor interation in the inhibition or rat liver steroid 5-α-reductase by 3-androstene-3-carboxylic acids;

3. *J. Med. Chem.* (1990) Vol. 33, pp. 943–950 (1990), by D. A. Holt, et al. describes the inhibition of steroid 5-α-reductase by unsaturated 3-carboxysteroids;

4. *J. Steroid Biochem*, Vol. 34, Nos. 1–6, pp. 571–575 (1989), by M. A. Levy, et al. describes the interaction mechanism between rat prostatic steroid 5-α-reductase and 3-carboxy-17β-substituted steroids;

5. *J. Med. Chem.* (1990) Vol. 33, pp. 937–942, by D. A. Holt, et al. describes the new steroid class of A ring aryl carboxylic acids;

6. *TIPS* (December 1989) Vol. 10, pp. 491–495, by D. W. Metcalf, et al. describes the effect of inhibitors of steroid 5-α-reductase in benign prostatic hyperplasia, male pattern baldness and acne; and 7. *EPO Publn. No.* 0 289 327, to D. A. Holt, et al. (SmithKline Beckman) describes steroidal 3-carboxylic acid derivatives as useful 5-α-reductase inhibitors.

8. *EPO Publn. No.* 0 343 954 A3, to D. A. Holt, et al., (SmithKline Beckman) describes steroidal 3-carboxylic acid derivatives as useful 5-α-reductase inhibitors.

9. *EPO Publn. No.* 0 465 142 A1, to G. H. Rasmusson, et al, (Merck & Co. Inc.) describes steroidal 3-carboxylic acid derivatives as useful 5-α-reductase inhibitors.

However, none of the above references specifically discloses or suggest that a steroid 5-α-reductase inhibiting compound would have utility in the treatment of cardiovascular disease.

It has now been discovered that steroid 5-α-reductase inhibitors are useful in the treatment of cardiovascular disease in mammals, including humans.

SUMMARY OF THE INVENTION

The present invention resides in the discovery that steroid 5-α-reductase inhibiting compounds are useful in treating cardiovascular disease in mammals, including humans. Included in the present invention are methods of co-administering a 5-α-reductase inhibiting compound with further active ingredients.

Also included in the present invention are combinations of steriod 5-α-reductase inhibitors and pharmaceutical compositions comprising a pharmaceutical carrier and a compound or a combination of compounds useful in the method of the invention.

DESCRIPTION OF THE INVENTION

An inhibitor of steriod 5-α-reductase, a combination of a steroid 5-α-reductase inhibitor and a further active ingredient or a combination of inhibitors of steroid 5-α-reductase are used in a pharmaceutical composition to treat cardiovascular disease in mammals, including humans.

Also included are derivatives of these compounds which may either give rise to the parent compounds in vivo or be useful themselves, such as pharmaceutically acceptable addition salts. Salts of these compounds containing a basic group are formed with organic or inorganic acids in the presence of a basic compound by methods known to the art. For example, the compound is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Examplary of the acid addition salts which are included in this invention are maleate, fumarate, lactate, oxalate, methane sulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethly)methylamine. Prodrug derivatives include 0-esters, especially the tri-0-lower alkanoly ester having from 2–8 carbon atoms in each alkanoyl group; 0-methly ethers or sulfate esters. Separated R and S stereoisomers are also useful.

Compounds that are considered to be steroid 5-α-reductase inhibitors include:

17β-(N-t-butylcarboxamide)-5-α-androst-1-ene-4-aza-3-one,

17β-(N-t-butylcarboxamide)-androst-3,5-diene-3-carboxylic acid or a salt thereof, 17β-(N,N-diisopropylcarboxamide)-androst-3,5-diene-3-carboxylic acid or a salt thereof, 17β-(N,N-diisopropylcarboxamide)-estra-1,3,5(10)-triene-3-carboxylic acid or a salt thereof.

17β-(N-t-butylcarboxamide)-estra-1,3,5(10)-triene-3-carboxylic acid or a salt thereof, 17β-(N,N-diisopropylcarboxamide)-estra-1,3,5(10)-triene-3-sulfonic acid or a salt thereof, 17β-(N-t-butylcarboxamide)-estra-1,3,5(10)-triene-3-sulfonic acid or a salt thereof, 17β-(N,N-diisopropylcarboxamide)-estra-1,3,5(10)-triene-3-phosphonic acid or a salt thereof, 17β-(N-t-butylcarboxamide)-estra-1,3,5(1O)-triene-3-phosphonic acid or a salt thereof, 17β-(N,N-diisopropylcarboxamide)-estra-1,3,5(10)-triene-3-phosphinic acid or a salt thereof, 17β-(N-t-butylcarboxamide)-estra-1,3,5(10)-triene-3-phosphinic acid or a salt thereof, 17β-(N-t-butylcarboxamide)-androst-3,5-diene-3-phosphinic acid or a salt thereof, 17β-(N,N-diisopropylcarboxamide)-androst-3,5-diene-3-phosphinic acid or a salt thereof, 17β-(N-t-butylcarboxamide)-androst-3,5-diene-3-phosphonic acid or a salt thereof, (Z)-17β-(N,N-diisopropylcarboxamide)-androst-4-ene-3-ylidene-acetic acid, 17β-(N,N-diisopropylcarboxamide)-5α-androst-2-ene-3-acetic acid, (Z)-17β-(N,N-diisopropylcarboxamide)-5α-androst-3-ylidene-acetic acid, 17β-(N,N-diisopropylcarboxamide)-5α-androst-3-ene-3-acetic acid, and 17β-(N-t-butylcarboxamide)-5α-androst-2-ene-3-acetic acid.

By the term "steroid 5-α-reductase inhibitor" and derivatives thereof as used herein is meant a compound which selectively inhibits the action of steroid 5-α-reductase in the conversion of T to DHT. As such, the use of a steroid 5-α-reductase inhibiting compound in vivo results in the depletion of DHT while maintaining normal T function.

Persons skilled in the art can readily determine if a compound is a specific steriod 5-α-reductase inhibitor by known methods, such as described in Levy et al., *J. Steroid Biochem.* 34:571–575, 1989. Additionally, the human 5-α-reductase enzyme, (and certain other mammalian 5-α-reductase enzymes), are known to exist in two isoforms, isozyme 1 and isozyme 2. As such, a specific inhibitor of 5-α-reductase can be a predominate inhibitor of isozyme 1 (hereinafter selective isozyme 1 inhibitor), a predominate inhibitor of isozyme 2 (hereinafter selective isozyme 2 inhibitor) or an inhibitor of both isozyme 1 and isozyme 2 (hereinafter a dual inhibitor). Persons skilled in the art can readily determine if a compound is a selective isozyme 1 inhibitor, selective isozyme 2 inhibitor or a dual inhibitor by known methods such as described in WO 93/23042, published 25 Nov. 1993. All such compounds are included within the scope of this invention.

By the term "treating" and derivatives thereof as used herein, is meant prophylatic or therapeutic therapy.

By the term "cardiovascular disease" as used herein includes arteriolosclerosis, hyperlipidemic syndrome, coronory spasm and/or atherosclerosis.

The term "hyperlipidemia" and the derivatives thereof as used in the specification and in the claims is meant the presence of an abnormally high level of lipids in the blood.

The term "antihyperlipidemic" as used herein is meant the lowering of excessive lipid concentrations to desired levels.

Preferred lipids, of which high levels thereof are treated by the presently invented methods, are; cholesterol, triglycerides, and low-density lipoproteins.

Arteriosclerosis and coronory spasm are treated by the presently invented methods as a result of selective DHT depletion with uncompromised T function. Selective DHT depletion prevents/curtails the inelasticity and vessel wall thickening, with lessened blood flow, associated with arteriosclerosis and prevents/curtails the inelasticity and thickening of heart muscle vessels associated with coronory spasm.

Atherosclerosis is treated by the presently invented methods as a result of selective DHT depletion with uncompromised T function. Physiologically, DHT is considered a growth promoter. Selective DHT depletion prevents/curtails the buildup of fatty deposits associated with atherosclerosis.

As used herein, when a 5-α-reductase inhibitor, as described herein and a further active ingredient or ingredients are utilized together, said 5-α-reductase inhibitor can be co-administered with said further active ingredient or ingredients.

By the term "co-administering" and derivatives thereof as used herein is meant either simultaneous administration or any manner of separate sequential administration of a 5-α-reductase inhibiting compound, as described herein, and a further active ingredient or ingredients, such as other compounds known to treat cardiovascular disease. Preferably, if the administration is not simultaneous, the compounds are administered in a close time proximity to each other. Furthermore, it does not matter if the compounds are administered in the same dosage form, e.g. one compound may be administered topically and another compound may be administered orally.

It has now been discovered that steroid 5-α-reductase inhibitors are useful in the treatment of cardiovascular disease in mammals, including humans.

While it is possible for the active ingredient(s) of the present invention to be administered alone, it is preferable to present it as a pharmaceutical formulation.

The compounds of the present invention are preferably incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the compounds of the present invention in a pharmaceutical dosage unit as described above will be an efficacious, nontoxic quantity preferably selected from the range of 0.01–1000 mg/kg of active compound, preferably 0.1–100 mg/kg. When treating a human patient in need of treatment for cardiovascular disease, the selected dose is administered preferably from 1–6 times daily, orally or parenterally. Preferred forms of parenteral administration include topically, rectally, transdermally, by injection and continuously by infusion. Oral dosage units for human administration preferably contain from 0.1 to 500 mg of active compound. Oral administration, which uses lower dosages is preferred. Parenteral administration, at high dosages, however, also can be used when safe and convenient for the patient.

The method of this invention of treating cardiovascular disease in mammals, including humans, comprises administering to a subject in need of such treatment an effective steroid 5-α-reductase inhibiting amount of a compound of the present invention.

The invention also provides for the use of a 5-α-reductase inhibiting compound in the manufacture of a medicament for use in treating cardiovascular disease.

The invention also provides for a pharmaceutical composition for use in the treatment of cardiovascular disease which comprises a 5-α-reductase inhibiting compound and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, particularly other compounds known to treat the cardiovascular disease. Particularly preferred is the co-administration of a 5-α-reductase inhibitor, as disclosed herein, and, acyl-CoA: cholesterol acyltransferase (ACAT) inhibitors, HMG CoA reductase inhibitors or bile acid sequestrants for use in the treatment of cardiovascular disease.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLE 1

An oral dosage form for administering the claimed compounds is produced by screening, mixing and filling into hard gelatin capsules the ingredients in the proportions shown in Table I below.

TABLE I

| INGREDIENTS | AMOUNTS |
|---|---|
| 17β-(N-t-butylcarboxamide)-androst-3,5-diene-3-carboxylic acid | 100 mg |
| Magnesium stearate | 5 mg |
| Lactose | 75 mg |

EXAMPLE II

The sucrose, calcium sulfate dihydrate and claimed compound shown in Table II below, are mixed and granulated in the proportions shown with a 10% gelatin solution. The wet granules are screened, dried, mixed with the starch, talc and stearic acid, screened and compressed into a tablet.

TABLE II

| INGREDIENTS | AMOUNTS |
|---|---|
| 17β-(N-t-butylcarboxamide)-androst-3,5-diene-3-carboxylic acid | 100 mg |
| Calcium sulfate dihydrate | 150 mg |
| Sucrose | 20 mg |
| Starch | 10 mg |
| Talc | 5 mg |
| Stearic Acid | 3 mg |

EXAMPLE III

17β-(N-t-butylcarboxamide)-androst-3,5-diene-3-carboxylic acid (1.0 g) is dissolved in 20 g of soybean oil and emulsified by mixing with 1.2 g of egg phospholipid and enough water to bring the final volume to 100 ml. The formed interlipid formulation is suitable for intravenous administration.

While the preferred embodiments of the invention are illustrated by the above, it is to be understood that the invention is not limited to the precise instructions herein disclosed and that the right to all modifications coming with the scope of the following claims is reserved.

What is claimed is:

1. A method of treating cardiovascular disease which comprises administering to a subject in need thereof an effective amount of a steroid 5-α-reductase inhibiting compound.

2. The method of claim 1 which comprises administering a dosage unit containing from about 0.1 mg to about 500 mg of said steroid 5-α-reductase inhibiting compound.

3. The method of claim 1 in which the steroid 5-α-reductase inhibiting compound is 17β-(N-t-butylcarboxamide)-androst-3,5-diene-3-carboxylic acid or a salt thereof.

4. The method of claim 1 in which the steroid 5-α-reductase inhibiting compound is:

17β-(N-t-butylcarboxamide)-5-α-androst-1-ene-4-aza-3-one,

17β-(N-t-butylcarboxamide)-androst-3,5-diene-3-carboxylic acid or a salt thereof, 17β-(N,N-diisopropylcarboxamide)-androst-3,5-diene-3-carboxylic acid or a salt thereof, 17β-(N,N-diisopropylcarboxamide)-estra-1,3,5(10)-triene-3-carboxylic acid or a salt thereof, 17β-(N-t-butylcarboxamide)-estra-1,3,5(10)-triene-3-carboxylic acid or a salt thereof, 17β-(N,N-diisopropylcarboxamide)-estra-1,3,5(10)-triene-3-sulfonic acid or a salt thereof, 17β-(N-t-butylcarboxamide)-estra-1,3,5(10)-triene-3-sulfonic acid or a salt thereof, 17β-(N,N-diisopropylcarboxamide)estra-1,3,5(10)-triene-3-phosphonic acid or a salt thereof, 17β-(N-t-butylcarboxamide)-estra-1,3,5(10)-triene-3-phosphonic acid or a salt thereof, 17β-(N,N-diisopropylcarboxamide)estra-1,3,5(10)-triene-3-phosphinic acid or a salt thereof, 17β-(N-t-butylcarboxamide)-estra-1,3,5(10)-triene-3-phosphinic acid or a salt thereof, 17β-(N-t-butylcarboxamide)-androst-3,5-diene-3-phosphinic acid or a salt thereof, 17β-(N,N-diisopropylcarboxamide)-androst-3,5-diene-3-phosphinic acid or a salt thereof, 17β-(N-t-butylcarboxamide)-androst-3,5-diene-3-phosphonic acid or a salt thereof, (Z)-17β-(N,N-diisopropylcarboxamide)-androst-4-ene-3-ylidene-acetic acid, 17β-(N,N-diisopropylcarboxamide)-5α-androst-2-ene-3-acetic acid, (Z)-17β-(N,N-diisopropylcarboxamide)-5α-androst-3-ylidene-acetic acid, 17β-(N,N-diisopropylcarboxamide)-5α-androst-3-ene-3-acetic acid, and 17β-(N-t-butylcarboxamide)-5α-androst-2-ene-3-acetic acid.

5. The method of claim 1 in which the steroid 5-α-reductase inhibiting compound is 17β-(N-t-butylcarboxamide)-5-α-androst-1-ene-4-aza-3-one.

6. The method of claim 1 in which the steroid 5-α-reductase inhibiting compound is 17β-(N-t-butylcarboxamide)-estra-1,3,5(10)-triene-3-carboxylic acid or a salt thereof.

7. The method of claim 1 in which the subject in need of treatment is a human.

8. A method of claim 1 in which the steroid 5-α-reductase inhibiting compound is a selective isozyme 1 inhibitor.

9. A method of claim 1 in which the steroid 5-α-reductase inhibiting compound is a selective isozyme 2 inhibitor.

10. A method of claim 1 in which the steroid 5-α-reductase inhibiting compound is a dual inhibitor.

11. A method of claim 1 in which the cardiovascular disease is arteriolosclerosis.

12. A method of claim 1 in which the cardiovascular disease is hyperlipidemia.

13. A method of claim 1 in which the cardiovascular disease is coronory spasm.

14. The method of claim 1 in which the cardiovascular disease is atherosclerosis.

* * * * *